United States Patent
Tanno

(10) Patent No.: US 12,414,745 B2
(45) Date of Patent: Sep. 16, 2025

(54) X-RAY IMAGING APPARATUS, TRAINED MODEL GENERATION METHOD, AND IMAGE PROCESSING METHOD

(71) Applicant: Shimadzu Corporation, Kyoto (JP)

(72) Inventor: Keiichi Tanno, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 244 days.

(21) Appl. No.: 17/926,774

(22) PCT Filed: Jul. 6, 2020

(86) PCT No.: PCT/JP2020/026452
§ 371 (c)(1),
(2) Date: Nov. 21, 2022

(87) PCT Pub. No.: WO2022/009281
PCT Pub. Date: Jan. 13, 2022

(65) Prior Publication Data
US 2023/0200760 A1   Jun. 29, 2023

(51) Int. Cl.
*A61B 6/12* (2006.01)
*A61B 6/00* (2006.01)

(52) U.S. Cl.
CPC . *A61B 6/12* (2013.01); *A61B 6/44* (2013.01)

(58) Field of Classification Search
CPC ........... A61B 6/12; A61B 6/44; A61B 6/4441; A61B 6/54
See application file for complete search history.

(56) References Cited

U.S. PATENT DOCUMENTS

2020/0043153 A1   2/2020   Tanno
2020/0297292 A1*  9/2020   Alexandroni ........ A61B 6/5294

FOREIGN PATENT DOCUMENTS

| JP | 2017-185007 A | 10/2017 | |
| JP | 2020-018702 A | 2/2020 | |
| WO | WO-2019017058 A1 * | 1/2019 | ............... A61B 6/00 |

OTHER PUBLICATIONS

Written Opinion by the International Searching Authority for PCT application No. PCT/JP2020/026452 dated Jul. 28, 2020, submitted with a machine translation.

* cited by examiner

*Primary Examiner* — Keith M Raymond
*Assistant Examiner* — Milton Truong
(74) *Attorney, Agent, or Firm* — Muir Patent Law, PLLC

(57) ABSTRACT

This X-ray imaging apparatus (100) is provided with an X-ray irradiation unit (2), an X-ray detection unit (3), a pulse width setting unit (72) for setting a pulse width of X-rays to be emitted, an X-ray irradiation control unit (71) for causing the X-rays to emit from the X-ray irradiation unit (2), an X-ray image generation unit (73) for generating an X-ray image (10), and a device detection unit (74) for detecting, based on a trained model (80) generated by machine learning, the device (200) reflected in the X-ray image (10). The pulse width is a blur suppression pulse width equal to or less than a pulse width at which detection accuracy of detecting the device (200) based on the trained model (80) is maximized.

11 Claims, 6 Drawing Sheets

X-RAY IMAGING APPARATUS, TRAINED MODEL GENERATION METHOD, AND IMAGE PROCESSING METHOD

TECHNICAL FIELD

The present invention relates to an X-ray imaging apparatus, a trained model generation method, and an image processing method.

BACKGROUND ART

Conventionally, a radiographic imaging apparatus for detecting a marker from a radiographic image using machine learning has been known. Such a radiographic imaging apparatus is disclosed in, for example, Japanese Unexamined Patent Application Publication No. 2017-185007.

The radiographic imaging apparatus described in the above-described Japanese Unexamined Patent Application Publication No. 2017-185007 is a device for capturing a radiographic image for imaging an inside of a subject by emitting radiation in a coronary intervention treatment. This radiographic imaging apparatus detects the position and the range of the marker for a radiographic image by image recognition from the radiographic image based on trained result data. The marker is provided as a marker for a stent of a catheter to be inserted into the body of the subject. The trained result data is acquired in advance by machine learning using a plurality of rotated images obtained by rotating an image including the marker at a plurality of angles. The radiographic imaging apparatus described in the above-described Japanese Unexamined Patent Application Publication No. 2017-185007 highlights and displays the stent reflected in the radiographic image based on the detected position of the marker.

PRIOR ART DOCUMENT

Patent Document

Patent Document 1: Japanese Unexamined Patent Application Publication No. 2017-185007

SUMMARY OF THE INVENTION

Problems to be Solved by the Invention

Here, although not described in the above-described Japanese Unexamined Patent Application Publication No. 2017-185007, it is conceivable to detect a medical device, such as, e.g., a catheter and a guidewire, which is not provided with a marker as a mark, in a radiographic image (X-ray image). In this case, it is conceivable to detect the device reflected in the X-ray image based on a trained model generated by machine learning.

However, a medical device, such as, e.g., a catheter and a guidewire, that is to be indwelled in a body of a subject moves irregularly due to the movements in the body of the subject, such as, e.g., a heartbeat. For example, in the case of capturing a plurality of X-ray images reflecting a medical device, such as, e.g., a catheter and a guidewire, indwelled in a coronary artery, the coronary artery moves (deforms) irregularly in accordance with the heartbeat. Therefore, the position and the shape of the medical device, such as, e.g., the catheter and the guidewire, vary irregularly in accordance with the heartbeat. Specifically, the moving speed of the coronary artery is small (approximately zero) when the heart expands most and when the heart contracts least. Therefore, the change in the position and the shape of the device is small. The moving speed of the coronary artery depends on the volume change rate of the heart between the time when the heart expands most and the time when the heart contracts least. Thus, the change in the position and the shape of the device becomes large.

As described above, the displacement (deformation) of the device within the body is not constant (i.e., irregular), and therefore, the device reflected in the captured X-ray image includes a blur of a wide variety of sizes. Therefore, a trained model needs to be trained to cope with a wide variety of blur to detect the device reflected in the X-ray image based on the trained model. That is, machine learning needs to be performed using a large number of training images to cope with a wide variety of blur. In this case, there is a case in which machine learning does not converge. Even in a case where machine learning converges, the detection accuracy of detecting the device based on the trained model generated by machine learning becomes low.

The present invention has been made to solve the above-described problems. It is an object of the present invention to provide an X-ray imaging apparatus, a trained model generation method, and an image processing method capable of accurately detecting a medical device indwelled in a body of a subject reflected in an X-ray image, based on a trained model generated by machine learning.

Means for Solving the Problems

In order to attain the above-described object, an X-ray imaging apparatus according to a first aspect of the present invention is provided with:
  an X-ray irradiation unit configured to irradiate a subject in which a medical device is indwelled with X-rays;
  an X-ray detection unit configured to detect the X-rays transmitted through the subject;
  a pulse width setting unit configured to set a pulse width of the X-rays emitted from the X-ray irradiation unit;
  an X-ray irradiation control unit configured to cause X-rays having the pulse width set by the pulse width setting unit to emit from the X-ray irradiation unit;
  an X-ray image generation unit configured to generate an X-ray image based on the X-rays detected by the X-ray detection unit, the X-rays having the set pulse width; and
  a device detection unit configured to detect the device in the X-ray image, based on a trained model generated by machine learning, from the X-ray image generated by the X-ray generation unit, the X-ray image being generated based on the X-rays having the set pulse width,
  wherein the pulse width is a blur suppression pulse width equal to or less than a pulse width at which detection accuracy of detecting the device based on the trained model is maximized.

A trained model generation method according to a second aspect of the present invention includes the steps of:
  acquiring a training input X-ray image, the training input X-ray image being generated to simulate a medical device to be indwelled in a body of a subject in an X-ray image generated based on the X-rays having a blur suppression pulse width equal to or less than a pulse width at which detection accuracy of detecting the medical device is maximized such that the training input X-ray image corresponds to the X-ray image generated based on the X-rays having the blur suppression pulse width;

acquiring training output information indicating a position or a shape of the device in the training input X-ray image; and generating a trained model by machine learning using the training input X-ray image and the training output information.

An image processing method according to a third aspect of the present invention includes the steps of:

setting a pulse width of X-rays emitted to generate an X-ray image to a blur suppression pulse width, the blur suppression pulse width being equal to or less than a pulse width at which detection accuracy of detecting a medical device indwelled in a body of a subject from the generated X-ray image based on a trained model generated by machine learning is maximized;

irradiating the subject in which the device is indwelled with the X-rays having the set blur suppression pulse width;

detecting the X-rays transmitted through the subject;

generating the X-ray image based on the detected X-rays having the blur suppression pulse width; and detecting the device in the X-ray image based on the trained model from the X-ray image generated based on the X-rays having the blur suppression pulse width.

Effects of the Invention

According to the X-ray imaging apparatus according to the first aspect of the present invention and the image processing method according to the third aspect of the present invention, the pulse width of the X-rays emitted to generate an X-ray image is set to a blur suppression pulse width that is equal to or less than a pulse width at which detection accuracy of detecting a medical device indwelled in a body of a subject from the generated X-ray image is maximized. Therefore, it is possible to detect the device based on the machine learning from the X-ray image generated based on the X-rays having the blur suppression pulse width. Therefore, the X-ray image is generated based on the X-rays having the blur suppression pulse width that is a relatively small pulse width equal to or less than a pulse width at which the detection accuracy of detecting the device is maximized. For this reason, even in a case where the device in the body of the subject irregularly moves due to irregular movements in the body, it is possible to suppress the increase in the number of blur type of the device reflected in the captured X-ray image. With this, even in a case where the device in the body of the subject moves irregularly, the blur of the device reflected in the X-ray image is suppressed to be smaller than a certain size. Therefore, it is possible to prevent the deterioration of the detection accuracy of detecting the device based on the trained model. Consequently, the medical device indwelled in the body of the subject in the X-ray image can be accurately detected based on the trained model generated by machine learning.

Further, in a case where the pulse width of the X-rays for generating an X-ray image is set to be larger than a pulse width at which the detection accuracy of detecting the device is maximized, the detection accuracy of detecting the device decreases. In a case where the pulse width is increased, the dose of X-rays irradiated to the subject also increases. On the other hand, in the present invention, an X-ray image is generated based on the X-rays having the blur suppression pulse width that is equal to or less than a pulse width at which the detection accuracy of detecting the device is maximized. Therefore, the X-ray image is generated based on the X-rays having the blur suppression pulse width, which are relatively small in the pulse width. For this reason, it is possible to suppress an increase in the dose of the X-rays emitted to the subject while effectively suppressing the decrease in the detection accuracy of detecting the device. As a consequence, the device can be detected with higher accuracy, and the dose of the X-rays emitted to the subject can be reduced.

Further, according to the trained model generation method according to the second aspect of the present invention, a training input X-ray image generated to simulate the device in the body of the subject reflected in the X-ray image generated based on the X-rays having the blur suppression pulse width is acquired. As a result, it is possible to suppress the increase in the number of blur type. Therefore, it is possible to suppress the acquisition of a large number of training input X-ray images to cope with a wide variety of blur type of the device. Here, in a case where machine learning is performed using a large number of training input X-ray images to correspond to X-ray images having a wide variety of blur, the learning is less likely to converge, and the detection accuracy by the trained model deteriorates even in a case where the machine learning converges. On the other hand, in the present invention, a training input X-ray image generated to simulate the device in the body of the subject reflected in the X-ray image generated based on the X-rays having the blur suppression pulse width is acquired. With such a configuration, as compared with the case where the pulse width is not restricted and therefore, the device blur in the image varies widely, the number of type of the X-ray image blur is reduced due to the X-rays having the blur suppression pulse width. Therefore, it is possible to reduce the number of blur type of the image acquired as a training image. As a result, it is possible to reduce the number of type of the training input X-ray image, which results in easy convergence of the machine learning as compared with the case where the blur type varies widely and also makes it possible to generate a trained model capable of detecting the device with high accuracy. Consequently, it is possible to provide a trained model generation method capable of accurately detecting the medical device indwelled in the body of the subject and reflected in the X-ray image.

EMBODIMENTS FOR CARRYING OUT THE INVENTION

Hereinafter, some embodiments in which the present invention is embodied will be described with reference to the attached drawings.

With reference to FIG. 1 to FIG. 11, the configuration of an X-ray imaging apparatus 100 according to one embodiment, an image processing method according to one embodiment, and a trained model generation method according to one embodiment will be described.

(Configuration of X-Ray Imaging Apparatus)

First, a configuration of an X-ray imaging apparatus 100 will be described with reference to FIG. 1 and FIG. 2.

Figure 1:
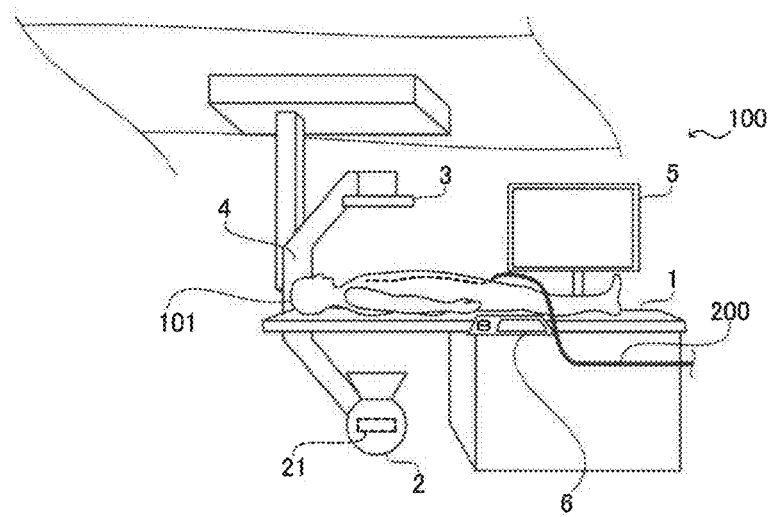
FIG. 1 is a schematic diagram showing the configuration of an X-ray imaging apparatus according to one embodiment.

As shown in FIG. 1, the X-ray imaging apparatus 100 is configured to irradiate a subject 101 in which a medical device 200 has been inserted into the body of the subject with X-rays. The X-ray imaging apparatus 100 performs X-ray imaging by detecting the X-rays transmitted through the subject 101. The X-ray imaging apparatus 100 generates an image for confirming the internal state of the body of the subject 101 when performing, for example, percutaneous coronary intervention (PCI: Percutaneous Coronary Intervention). The percutaneous coronary intervention is a treatment for eliminating stenosis and occlusion of a blood vessel of a heart using a device 200 for angina and myocardial infarction, which are diseases caused by stenosis and occlusion of coronary arteries.

(Device)

The device 200 is indwelled in the body of the subject 101. The device 200 includes, for example, a catheter or a guidewire to be indwelled in a blood vessel in the vicinity of a heart of the subject 101. The device 200 is formed of a flexible material that is movable to be insertable into a blood vessel of a human body. That is, the device 200 is inserted into the blood vessel of the subject 101 while changing its shape in accordance with the shape of the blood vessel of the subject 101. The device 200 is deformed in accordance with the movements of the blood vessel caused by the movements within the body of the subject 101. The movements within the body of the subject 101 include, for example, the heartbeat and the deformations of the blood vessel due to the blood flow. That is, the device 200 moves largely three-dimensionally in an irregular manner due to the heartbeat in the blood vessel in the vicinity of the heart. Here, the term "blood vessel in the vicinity of the heart" includes not only a blood vessel near the heart but also a blood vessel of the heart itself (coronary artery, etc.).

In percutaneous coronary intervention, the device 200 is used to place a treatment device, such as, e.g., a stent, to be indwelled at a stenotic site in the blood vessel (coronary artery) of the subject 101, at a target position in the blood vessel. The device 200 is inserted from a blood vessel (such as, e.g., radial artery or femoral artery) of a wrist or a thigh to a stenotic site of a coronary artery. In percutaneous coronary intervention, a stent is placed at the stenotic site of the coronary artery by the device 200 inserted into the blood vessel. Then, a treatment is performed on the stenosis of the blood vessel by expanding the stent.

(X-Ray Imaging Apparatus)

Figure 2:
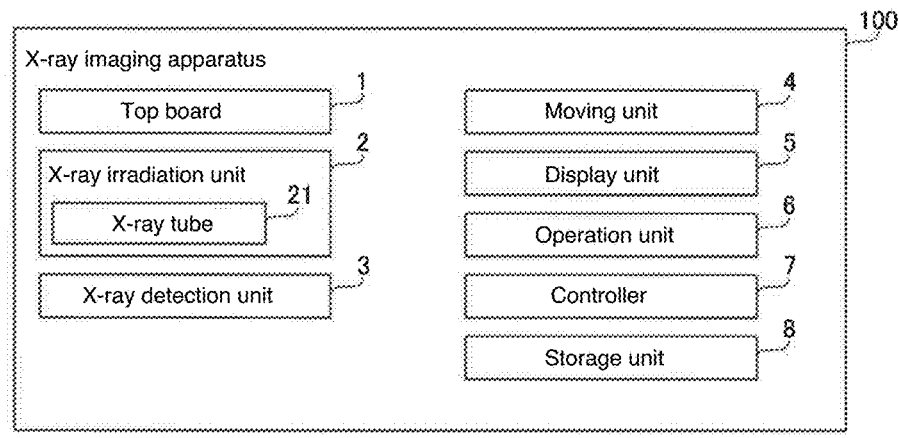
FIG. 2 is a block diagram showing the configuration of the X-ray imaging apparatus according to one embodiment.

As shown in FIG. 2, the X-ray imaging apparatus 100 is provided with a top board 1, an X-ray irradiation unit 2, an X-ray detection unit 3, a moving unit 4, a display unit 5, an operation unit 6, a controller 7, and a storage unit 8.

The top board 1 is configured to place a subject 101 to be irradiated with X-rays thereon. In a state in which the subject 101 is placed on the top board 1, the device 200 is inserted into the subject 101, and X-ray imaging is performed. The top board 1 is configured to be movable by a top board moving unit (not shown) under the control of the controller 7.

The X-ray irradiation unit 2 emits X-rays to the subject 101 in which the medical device 200 is indwelled. The X-ray irradiation unit 2 includes an X-ray tube 21 that emits X-rays when a voltage is applied. The X-ray tube 21 is configured such that the X-rays to be emitted are controlled when the voltage applied to the X-ray tube 21 is controlled by the controller 7. The X-ray irradiation unit 2 emits X-rays once or a plurality of times to the device 200 in the subject 101.

The X-ray detection unit 3 detects the X-rays transmitted through the subject 101. The X-ray detection unit 3 outputs a detection signal based on the detected X-rays. The X-ray detection unit 3 includes, for example, an FPD (flat panel detector).

The moving unit 4 holds the X-ray irradiation unit 2 and the X-ray detection unit 3 in a moveable manner. Specifically, the moving unit 4 supports the X-ray irradiation unit 2 and the X-ray detection unit 3 to face each other across the top board 1 on which the subject 101 is placed. The moving unit 4 supports the X-ray irradiation unit 2 and the X-ray detection unit 3 such that the position and the angle of the X-ray irradiation unit 2 and the X-ray detection unit 3 with respect to the subject 101 can be changed. The moving unit 4 supports the X-ray irradiation unit 2 and the X-ray detection unit 3 such that the distance between the X-ray irradiation unit 2 and the X-ray detection unit 3 can be changed. That is, the moving unit 4 moves the X-ray irradiation unit 2 and the X-ray detection unit 3 to perform X-ray imaging from various positions at various angle with respect to the subject 101.

The display unit 5 is, for example, a monitor, such as, e.g., a liquid crystal display. The display unit 5 displays images (a still image and a moving image) generated based on the controller 7.

The operation unit 6 is configured to accept an input operation for operating the X-ray imaging apparatus 100. The operation unit 6 accepts, for example, an operation of moving the top board 1 and the moving unit 4. The operation unit 6 receives an operation for irradiating the subject 101 with X-rays when performing X-ray imaging. Further, the operation unit 6 accepts an input operation for executing the control by the controller 7.

Figure 3:
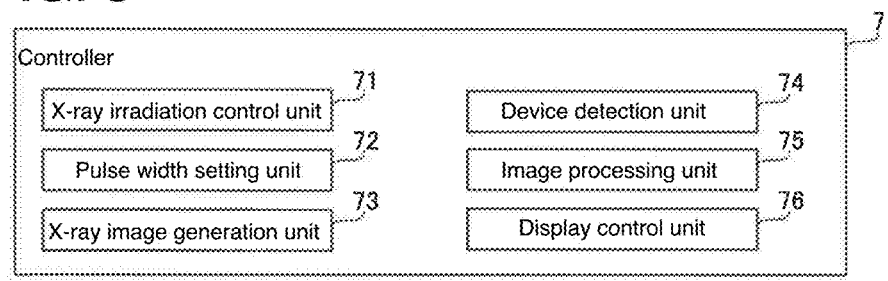
FIG. 3 is a diagram for explaining the functional configuration of a controller according to one embodiment.

The controller 7 is a computer including a CPU (Central Processing Unit), a GPU (Graphics Processing Unit), an ROM (Read Only Memory), and an RAM (Random Access Memory). The controller 7 performs the control of each unit of the X-ray imaging apparatus 100, the control of generating the X-ray image 10, and the control of image-processing on the generated X-ray image 10 by the CPU executing a predetermined control program. Specifically, as shown in FIG. 3, the controller 7 includes, as functional configurations, an X-ray irradiation control unit 71, a pulse width setting unit 72, an X-ray image generation unit 73, a device detection unit 74, an image processing unit 75, and a display control unit 76. That is, the controller 7 functions as the X-ray irradiation control unit 71, the pulse width setting unit 72, the X-ray image generation unit 73, the device detection unit 74, the image processing unit 75, and the display control unit 76 by the CPU executing predetermined control programs. The detailed control by the controller 7 will be described later.

The storage unit 8 is configured by a storage device, such as, e.g., a hard disk drive. The storage unit 8 is configured to store image data, imaging conditions, and various setting values. The storage unit 8 is storing a program for causing the controller 7 to function. The storage unit 8 stores a trained model 80 (see FIG. 8) generated by machine learning in advance.

(Control of X-Ray Imaging Apparatus By Controller)

The X-ray irradiation control unit 71 of the controller 7 controls the X-ray irradiation unit 2 and the X-ray detection unit 3 to perform X-ray imaging. The X-ray irradiation control unit 71 controls the X-ray radiation by the X-ray irradiation unit 2. Specifically, the X-ray irradiation control unit 71 causes the X-rays having a pulse width set by the pulse width setting unit 72 described later to be emitted from the X-ray irradiation unit 2. In particular, the X-ray irradiation control unit 71 controls the pulse width of the X-rays emitted from the X-ray tube 21 by controlling the voltage applied to the X-ray tube 21. The pulse width means the irradiation time (exposure time) during which the subject 101 is irradiated with X-rays to capture one X-ray image 10. The X-ray irradiation control unit 71 performs the control to move the moving unit 4. Further, the X-ray irradiation control unit 71 acquires the operation signal based on the input operation received by the operation unit 6 and controls each unit of the X-ray imaging apparatus 100 based on the acquired operation signal. For example, the X-ray irradiation control unit 71 moves the positions of the X-ray irradiation unit 2 and the X-ray detection unit 3 for performing X-ray imaging by controlling the moving unit 4 based on the input operation to the operation unit 6.

The pulse width setting unit 72 sets a pulse width of X-rays to be emitted from the X-ray irradiation unit 2 to the subject 101. In this embodiment, the pulse width setting unit 72 sets the pulse width of the X-rays to be emitted to a blur suppression pulse width that is equal to or less than a pulse width at which the detection accuracy of detecting the device 200 based on the trained model 80 to be described later is maximized. The pulse width setting unit 72 may set the pulse width based on the input operation to the operation unit 6, or may set the pulse width based on the pulse width set value stored in advance in the storage unit 8. The blur suppression pulse width will be detailed later.

Figure 4:
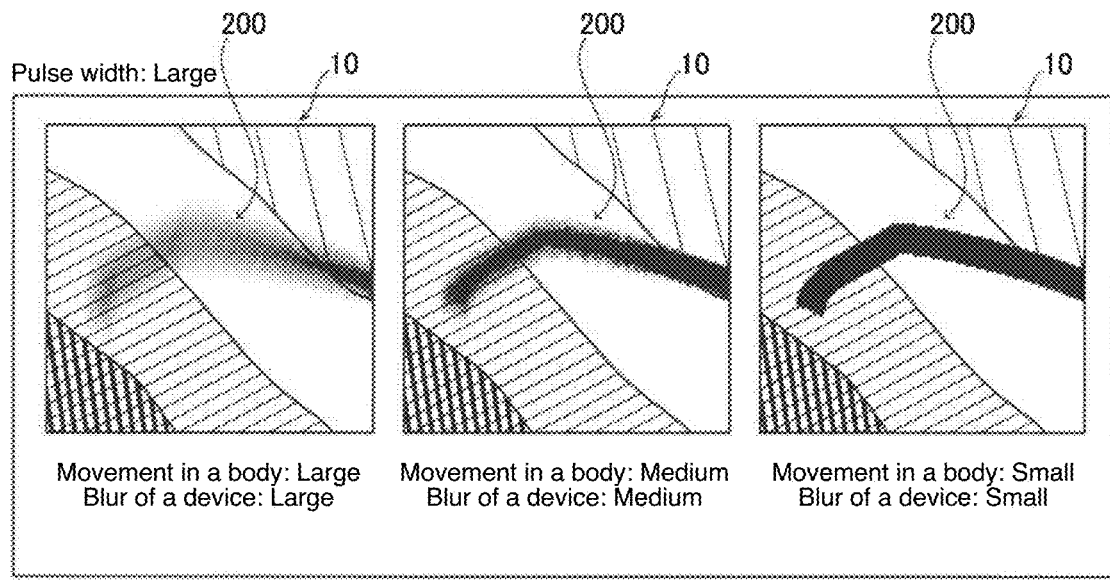
FIG. 4 is a diagram for explaining an X-ray image having a large pulse width.
Figure 5:
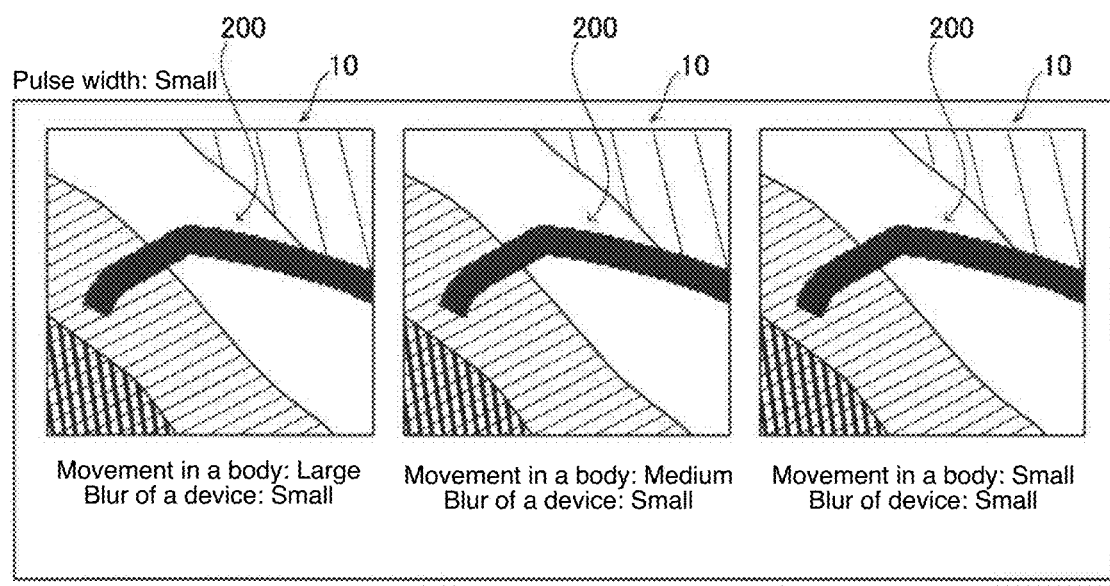
FIG. 5 is a diagram for explaining an X-ray image having a small pulse width.

The X-ray image generation unit 73 of the controller 7 generates an X-ray image 10 by performing X-ray imaging as shown in FIG. 4 and FIG. 5. In this embodiment, the X-ray image generation unit 73 generates the X-ray image 10 based on the X-rays detected by the X-ray detection unit 3. Specifically, the X-ray image generation unit 73 generates the X-ray image 10 by using the X-rays having a blur suppression pulse width, based on the detection signal from the X-ray detection unit 3.

Here, the X-ray image 10 shown in FIG. 4 is an X-ray image 10 captured using X-rays having a relatively large pulse width. The X-ray image 10 shown in FIG. 5 is an X-ray image 10 captured using X-rays having a relatively small pulse width. As will be apparent from the above, in the X-ray image 10 captured using X-rays having a relatively large pulse width, the device 200 reflected in the X-ray image 10 includes a large blur when the movements within the body of the subject 101 are large, and includes a small blur when the movements within the body of the subject 101 are small. That is, in the X-ray image 10 captured using X-rays having a relatively large pulse width, the device 200 includes a wide variety of blur. On the other hand, in the X-ray image 10 captured using X-rays having a relatively small pulse width, the device 200 reflected in the X-ray image 10 includes a small blur in both the case where the movements within the body of the subject 101 are large and the case where the movements within the body of the subject 101 are small. That is, regardless of the movement amount (moving speed) of the movements within the body of the subject 101, the magnitude of the blur decreases (becomes constant). For example, in a case where a catheter or a guidewire indwelled in the blood vessel in the vicinity of the heart of the subject 101 is imaged, the catheter or the guidewire reflected in the generated X-ray image 10 moves (deforms) irregularly due to the heartbeat of the subject 101. The movements of the subject 101 within the body, such as a heartbeat, is not constant. Thus, as shown in FIG. 4, the X-ray image 10 captured using X-rays having a relatively large pulse width will be an image containing a wide variety of blur. On the other hand, as shown in FIG. 5, in the X-ray image 10 captured using X-rays having a relatively small pulse width, the type (size) of blur is reduced even if the inside of the body of the subject 101 moves (deforms) irregularly like a heartbeat.

In this embodiment, the X-ray irradiation control unit 71 causes the X-rays having a blur suppression pulse width that is a pulse width equal to or less than a predetermined threshold to emit from the X-ray irradiation unit 2 in order to suppress a wide variety of blur of the device 200 including a catheter or a guidewire reflected in the generated X-ray image 10. That is, one emission of X-rays for generating one X-ray image 10 is an emission of X-rays having a pulse width (exposure time) equal to or less than a predetermined threshold. Further, the X-ray image 10 generated based on the X-rays having a blur suppression pulse width is an X-ray image 10 with a small dose due to the small pulse width. Further, the X-ray image 10 generated based on X-rays having the blur suppression pulse width becomes an image with a small blur type. The predetermined threshold and the blur suppression pulse width will be detailed later.

(Generation of Enhanced Image By Controller)

Figure 6:
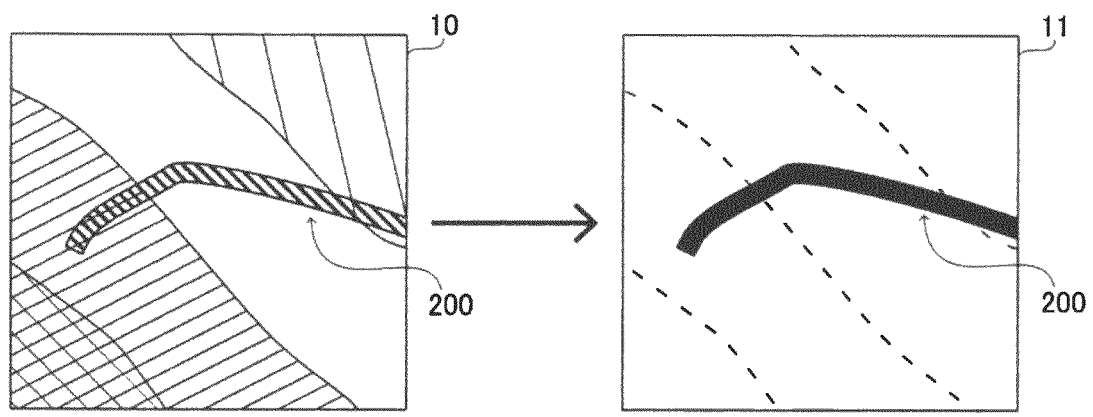
FIG. 6 is a diagram for explaining the generation of an enhanced image.

The device detection unit 74 of the controller 7 is configured to detect the device 200 from the X-ray image 10 generated based on the X-rays having the blur suppression pulse width, based on the trained model 80 generated by machine learning using an image generated to correspond to a blur suppression pulse width as a training image. The image processing unit 75 of the controller 7 generates an enhanced image 11 in which the device 200 is emphasized by performing image processing for emphasizing the device 200 detected in the X-ray image 10. That is, as shown in FIG. 6, the controller 7 (the device detection unit 74 and the image processing unit 75) generates the enhanced image 11 in which the device 200 is high in resolution from the X-ray image 10 in which the device 200 is low in resolution.

The trained model 80 is stored in advance in the storage unit 8. The trained model 80 is generated in advance by machine learning for learning the process of detecting the position of the device 200 from the input X-ray image 10. The generation of the trained model 80 will be detailed later.

The device detection unit 74 of the controller 7 detects the position of the device 200 reflected in the X-ray image 10 from the generated X-ray image 10 based on the trained model 80 to acquire the position information of the device 200 included in the X-ray image 10. Then, the device detection unit 74 determines the area of the device 200 and the area of the background that is not the device 200 out of the X-ray image 10, based on the acquired position information. Further, the processing unit 75 of the controller 7 performs image processing for increasing the density on the area in the X-ray image 10 determined to be the device 200 in the X-ray image. Further, the image processing unit 75 performs image processing for reducing the density on the area in the X-ray image 10 determined to be a background other than the device 200 in the X-ray image 10. In this way, the controller 7 (the device detection unit 74 and the image processing unit 75) acquires the position information of the device 200 based on the trained model 80 and generates the enhanced image 11 in which the device 200 is enhanced based on the acquired position information.

Figure 7:
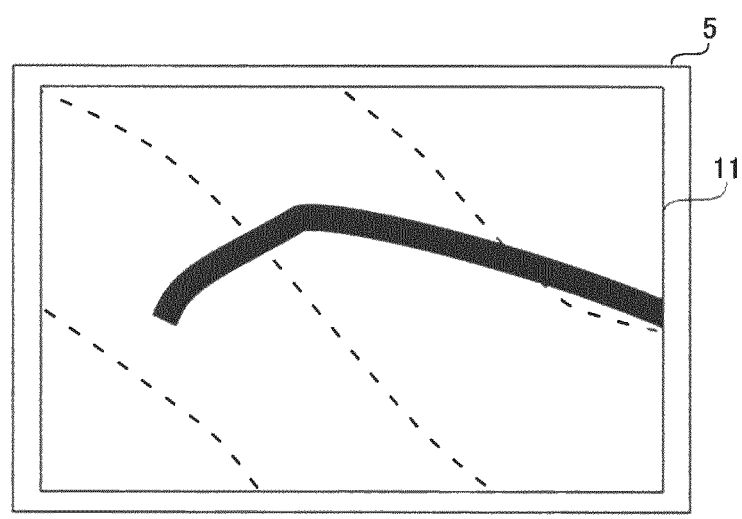
FIG. 7 is a diagram for explaining the display of a display unit.

As shown in FIG. 7, the display control unit 76 of the controller 7 controls the display of the display unit 5. Specifically, the display control unit 76 causes the display unit 5 to display the generated enhanced image 11. For example, the controller 7 causes the X-ray irradiation unit 2 to emit X-rays 15 times per second by the X-ray irradiation control unit 71 to thereby generate 15 frames of X-ray images 10 per second by the X-ray image generation unit 73. Then, 15 frames of enhanced images 11 are generated per second by the image processing unit 75 of the controller 7 from the generated X-ray images 10. Then, the display control unit 76 causes the enhanced image 11 generated in real time to be displayed on the display unit 5 as a moving image of 15 FPS (frames per second). Note that the controller 7 (display control unit 76) may be configured to cause the enhanced image 11, which is a single still image, to be displayed on the display unit 5.

(Generation of Trained Model)

Figure 8:
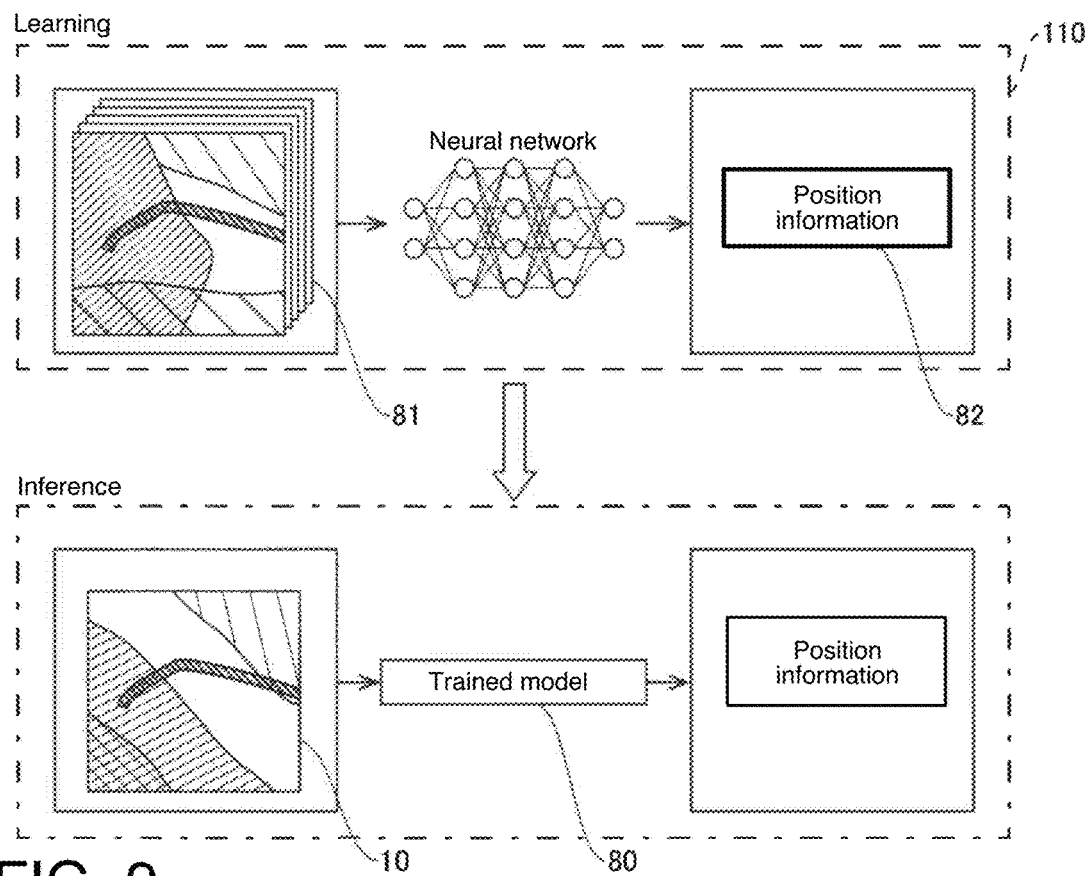
FIG. 8 is a diagram for explaining the generation of a trained model.

As shown in FIG. 8, the trained model 80 is generated by machine learning using a training image corresponding to the X-ray image 10 generated based on the X-rays having the blur suppression pulse width. Specifically, the trained model 80 is generated by machine learning using training input X-ray images 81 and training output information 82. The training input X-ray image 81 is generated to simulate the device 200 in the body of the subject 101 reflected in the X-ray image 10 generated based on the X-rays having the blur suppression pulse width. The training output information 82 indicates the position (coordinate) of the device 200 included in the training input X-ray image 81. The training input X-ray image 81 is generated to simulate the device 200 in the body of the subject 101, based on the simulated X-ray image generated based on the X-rays having the blur suppression pulse width. The trained model 80 is generated in advance by the learning device 110, which is separate from the X-ray imaging apparatus 100.

The learning device 110 is a computer for machine learning, including, for example, a CPU, a GPU, a ROM, and a RAM.

Figure 9:
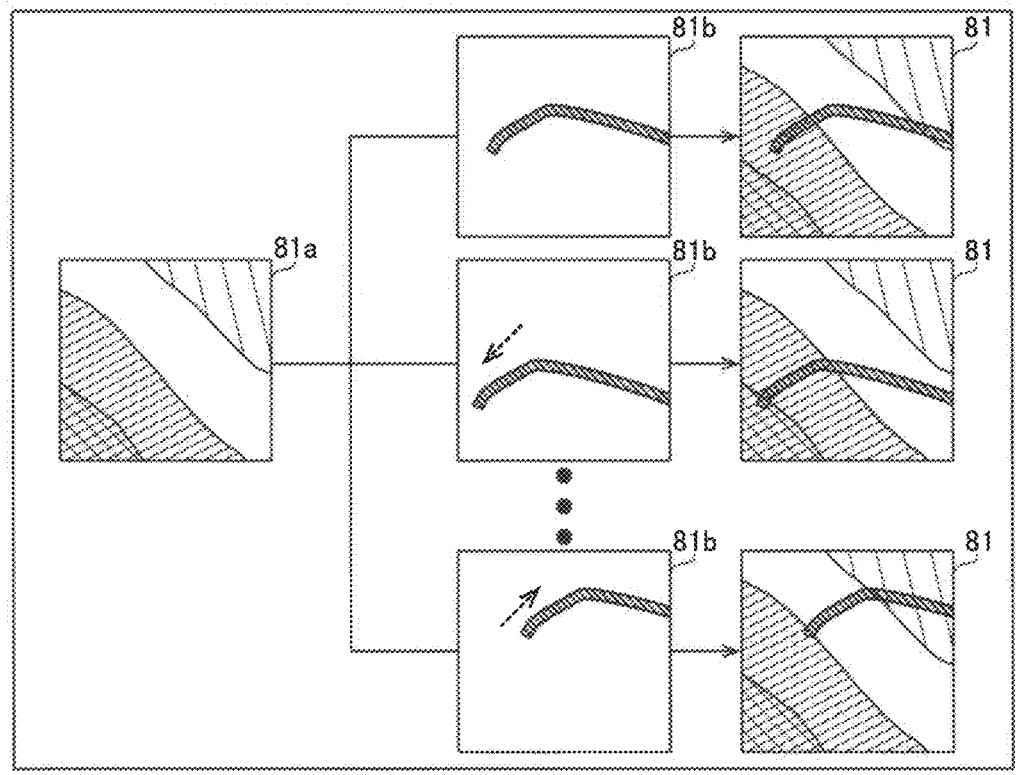
FIG. 9 is a diagram for explaining the generation of a training input X-ray image.

As shown in FIG. 9, the learning device 110 acquires a simulated X-ray image acquired by simulatively imaging the subject 101 and the device 200 indwelled in the body of the subject 101 by using the X-rays having a blur suppression pulse width that is a pulse width equivalent to the pulse width used when generating the X-ray image 10 by the X-ray imaging apparatus 100. The simulated X-ray image includes, for example, a simulated human body image 81a acquired by X-ray-imaging a human body model simulating a subject 101 with the X-rays having the blur suppression pulse width, and a simulated device image 81b acquired by imaging the device 200 indwelled in the body of the subject 101 with the X-rays having the blur suppression pulse width.

The learning device 110 simulates the movements of the device 200 in the body of the subject 101 by performing image processing on the acquired simulated X-ray images (the simulated human body image 81a and the simulated device image 81b). Specifically, the learning device 110 generates a plurality of training input X-ray images 81 to simulate the device 200 in the body of the subject 101 reflected in the X-ray images 10 by synthesizing a plurality of simulated device images 81b to which image processing has been performed to simulate the movements of the device 200 in the body of the subject 101 and the acquired simulated human body image 81a. In detail, the learning device 110 simulates for one simulated device image 81b by performing image processing while changing a plurality of parameters, thereby generating a plurality of simulated device images 81b to which image processing has been performed. Then, the learning device 110 generates a plurality of training input X-ray images 81 by synthesizing the plurality of simulated device images 81b and the simulated human body image 81a to which the image-processing has been performed while changing a plurality of parameters. The plurality of parameters includes the movements of the body of the subject 101 (such as a heartbeat) in a period (a period corresponding to the irradiation time of the X-rays having the blur suppression pulse width) that is equal to or less than a predetermined threshold, the site of the human body to be irradiated with the X-rays, the angle at which the X-rays are emitted, and the like. Further, the learning device 110 acquires a plurality of simulated device images 81b and a plurality of simulated human body images 81a while changing the pulse width of the X-rays within the range (the range of the blur suppression pulse width) of a predetermined threshold or less. Further, the learning device 110 performs simulation for the plurality of acquired simulated device images 81b and a plurality of simulated human body images 81a, by performing image processing while changing a plurality of parameters, thereby generating a plurality of training input X-ray images 81 corresponding to various sites of the subject 101 and various imaging conditions. That is, an X-ray image having a pulse width larger than the predetermined threshold is not included in the training input X-ray image 81.

Further, the learning device 110 detects the position of the device 200 (the area where the device 200 is located) as the position information from the acquired simulated device image 81b to acquire the position information of the device 200 in the corresponding training input X-ray image 81 as the training output information 82. The position information includes, for example, the coordinates of the pixels corresponding to the device 200 among the pixels constituting the training input X-ray image 81.

The learning device 110 performs learning by machine learning using the training input X-ray image 81 as an input and the training output information 82 as an output to generate the trained model 80. That is, the learning device 110 causes the trained model 80 to be learned by machine learning using the training input X-ray image 81 and the training output information 82 as training data (training set). The learning device 110 generates a trained model 80 using the training input X-ray image 81 generated from a plurality of types of simulated X-ray images. As the machine learning method, deep learning, which is machine learning using a multi-layer neural network, is used. A machine learning method is, for example, deep learning using a fully convolutional neural network (Fully Convolutional Networks: FCN).

The generated trained model 80 is provided to the X-ray imaging apparatus 100 via a network, or in a state of being stored in a recording medium, such as, e.g., a flash memory.
(Blur Suppression Pulse Width)

Figure 10:
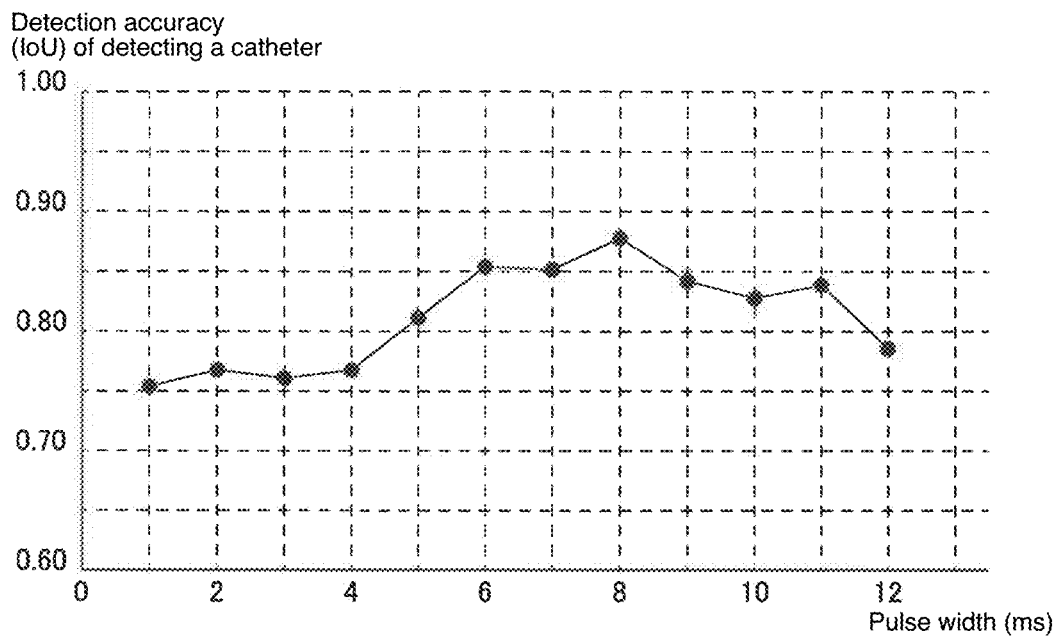
FIG. 10 is a diagram for explaining the relation between a pulse width of X-rays and detection accuracy of detecting a catheter.
Figure 11:
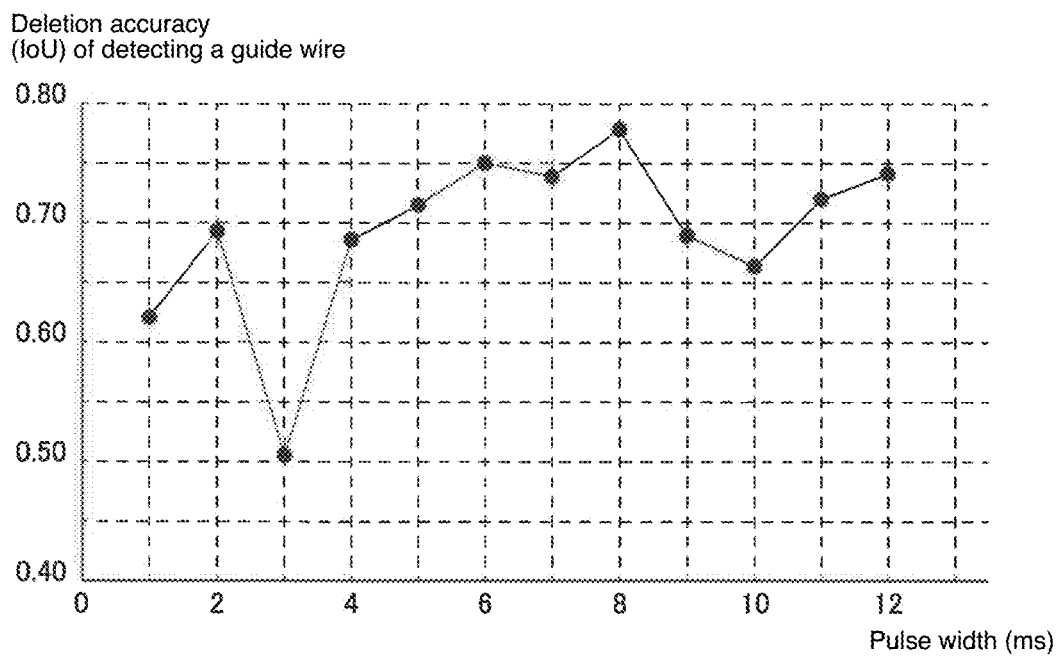
FIG. 11 is a diagram for explaining the relation between a pulse width of X-rays and detection accuracy of detecting a guidewire.

Here, as shown in FIG. 10 and FIG. 11, the detection accuracy (IoU: Intersection over Union) of detecting the device 200 according to the trained model 80 differs depending on the pulse width of the X-rays for capturing the X-ray image 10. That is, as the pulse width increases, the image of the device 200 reflected in the captured image increases in the type of blur due to the movements (e.g., the heartbeat) of the subject 101 in the body of the subject 101. On the other hand, as the pulse width of the X-rays becomes smaller, the dose of the emitted X-rays decreases, and therefore, the captured images become unclear. Therefore, the detection accuracy of detecting the device 200 using the trained model 80 decreases both in a case where the pulse width of X-rays is too large and in a case where the pulse width of X-rays is too small. For this reason, the detection accuracy of detecting the device 200 based on the trained model 80 has an upwardly convex change as the pulse width increases. For example, the trained model 80 has the highest detection accuracy of detecting the device 200 in the X-ray image 10 generated based on the X-rays having a pulse width of 8 milliseconds (ms).

For example, as shown in FIG. 10, in the case of detecting a catheter, which is a device 200, reflected in the X-ray image 10 using the trained model 80, the detection accuracy of detecting the catheter (device 200) becomes highest when the pulse width is 8 milliseconds (ms). Further, as shown in FIG. 11, in the case of detecting a guidewire, which is a device 200, reflected in the X-ray image 10 using the trained model 80, similarly, the detection accuracy of detecting the guidewire (device 200) becomes highest when the pulse width is 8 milliseconds (ms).

Note that the detection accuracy (IoU: Intersection over Union) of detecting the device 200 using the trained model 80 represents the degree of coincidence between the position information of the device 200 outputted when the training input X-ray image 81 is inputted to the trained model 80 generated based on the learning device 110 and the corresponding training output information 82.

The blur suppression pulse width of the X-rays when capturing the X-ray image 10 in the X-ray imaging apparatus 100 is determined based on the detection accuracy of detecting the device 200 using the trained model 80. In this embodiment, the blur suppression pulse width is a pulse width equal to or less than a pulse width at which the detection accuracy of detecting the device 200 reflected in the X-ray image 10 based on the trained model 80 is maximized. For example, the predetermined threshold is 8 milliseconds (ms). That is, the blur suppression pulse width is a pulse width of 8 milliseconds (ms) or less.

For example, in a case where a blur suppression pulse width is set to a pulse width of 5 milliseconds (ms) to perform the X-ray imaging of the subject 101, the X-ray imaging apparatus 100 irradiates the subject 101 with the X-rays having a pulse width of 5 milliseconds (ms) to generate the X-ray image 10. Further, the X-ray imaging apparatus 100 generates the enhanced image 11 from the generated X-ray image 10 based on the trained model 80 generated using a plurality of simulated X-ray images (simulated human body images 81a and simulated device images 81b) generated based on the X-rays having a pulse width within a range of 8 milliseconds (ms) or less. Note that in the X-rays having the blur suppression pulse width, the irradiation time (pulse width) can be appropriately changed within a range of 8 milliseconds (ms) or less (equal to or less than a predetermined value).

As described above, the X-ray imaging apparatus 100 generates the X-ray image 10 generated based on the X-rays having a blur suppression pulse width by emitting the X-rays having the blur suppression pulse width that is a pulse width equal to or less than a predetermined threshold at which the detection accuracy of detecting the device 200 reflected in the X-ray image 10 based on the trained model 80 becomes highest. Then, the X-ray imaging apparatus 100 acquires the position information (area) of the device 200 among the generated X-ray images 10, based on the trained model 80 generated to correspond to the blur suppression pulse width by machine learning using the simulated human body image 81a generated based on the X-rays having the blur suppression pulse width and the simulated device image 81b generated based on the X-rays having the blur suppression pulse width.
(Generation Method of Trained Model by this Embodiment)

Figure 12:
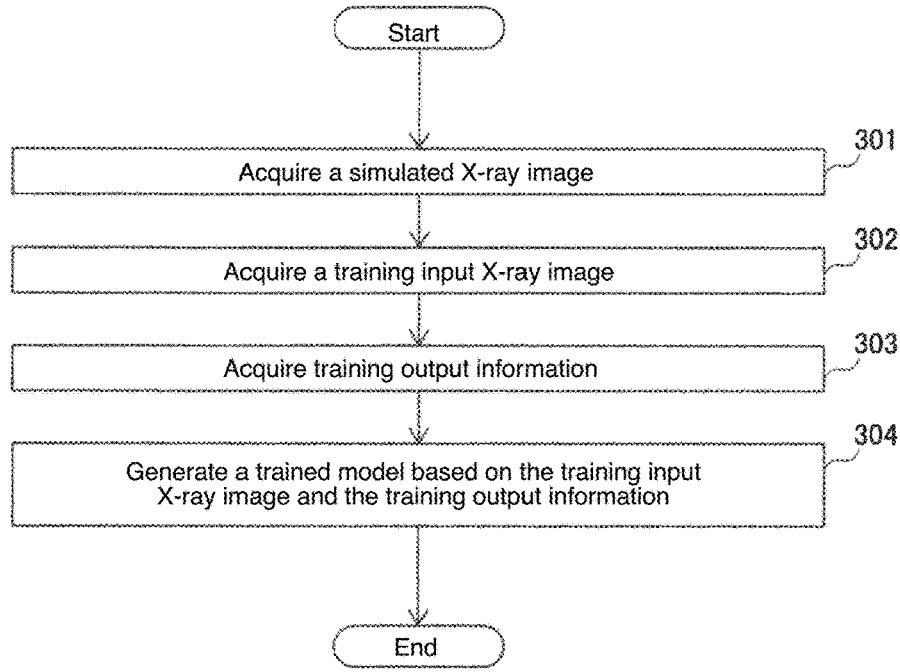
FIG. 12 is a flowchart for explaining a trained model generation method according to one embodiment.

Next, with reference to FIG. 12, the generation method of the trained model according to this embodiment will be described. Note that the generation method of the trained model is performed by the learning device 110.

First, in Step 301, a simulated X-ray image generated based on the X-rays having the blur suppression pulse width is acquired. That is, a simulated X-ray image is acquired in which the simulated human body image 81a acquired by X-ray-imaging a human phantom with the X-rays having the blur suppression pulse width and a simulated device image 81b acquired by X-ray-imaging the device 200 indwelled in the body of the subject 101 by using the X-rays having the blur suppression pulse width are included.

Next, in Step 302, image processing is performed on the acquired simulated device image 81b. Then, the image processed simulated device image 81b and the acquired simulated human body image 81a are synthesized. That is, image processing is performed on the acquired simulated X-ray image to thereby acquire a plurality of training input X-ray images 81 generated to simulate the device 200 in the body of the subject 101 reflected in the X-ray image 10 generated based on the X-rays having the blur suppression pulse width. That is, based on the acquired simulated X-ray images (the simulated human body image 81a and the simulated device image 81b), a plurality of training input X-ray images 81 generated to correspond to the X-ray image 10 generated based on the X-rays having the blur suppression pulse width equal to or less than a pulse width at which the detection accuracy of detecting the medical device 200 indwelled in the body of the subject 101 is maximized is acquired.

Next, in Step 303, the training output information 82 indicating the position of the device 200 reflected in the training input X-ray image 81 is acquired based on the acquired simulated X-ray image.

Next, in Step 304, the trained model 80 is generated (learned) by machine learning using the training input X-ray image 81 as an input and the training output information 82 as an output.

Note that either the step of acquiring the training input X-ray image 81 in Step 302 or the step of acquiring the training output information 82 in Step 303 may be performed first.
(Image Processing Method by this Embodiment)

Figure 13:
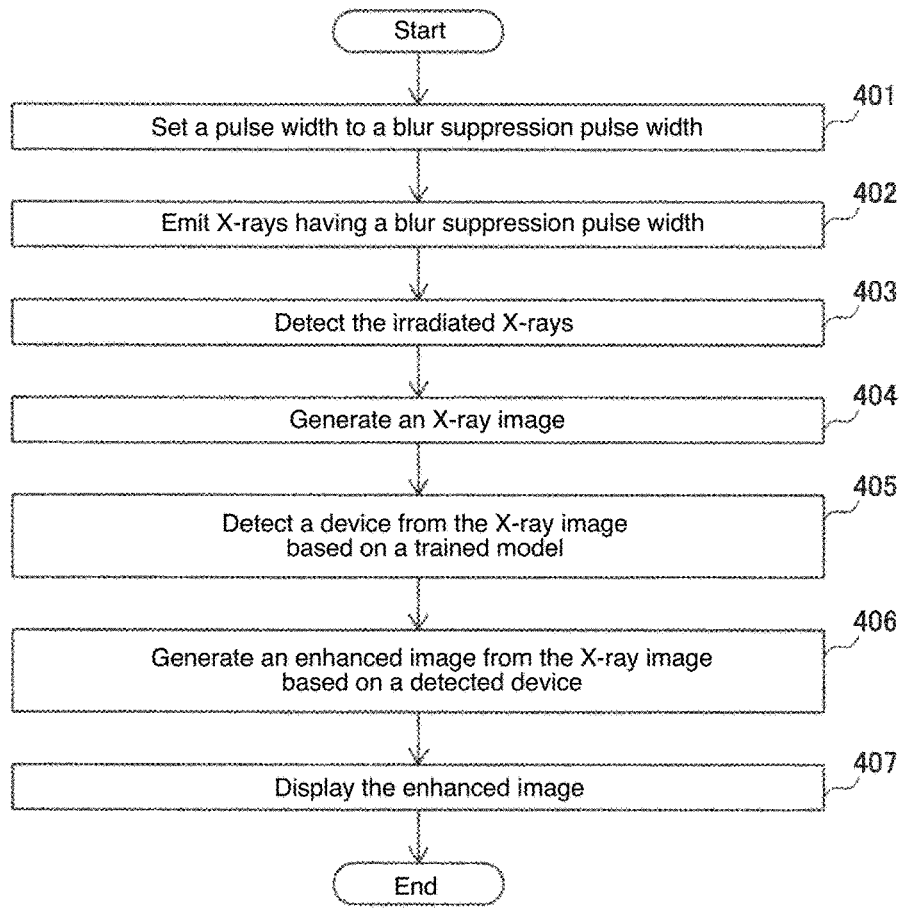
FIG. 13 is a flowchart for explaining an image processing method according to one embodiment.

Next, the image processing method by this embodiment will be described with reference to FIG. 13. The image processing method is performed by the controller 7 of the X-ray imaging apparatus 100.

First, in Step 401, based on the trained model 80 generated by machine learning, the pulse width of the X-rays emitted to generate the X-ray image 10 is set to the blur suppression pulse width that is a pulse width at which the detection accuracy of detecting the medical device 200 indwelled in the body of the subject 101 from the generated X-ray image 10 is maximized. Specifically, in order to emit the X-rays having the blur suppression pulse width, the pulse width of the X-rays emitted from the X-ray irradiation unit 2 is set to the blur suppression pulse width by the pulse width setting unit 72.

Next, in Step 402, the subject 101 in which the medical device 200 is indwelled is irradiated with the X-rays having the set blur suppression pulse width by the X-ray irradiation unit 2.

Next, in Step 403, the X-rays having the blur suppression pulse width transmitted through the subject 101 are detected by the X-ray detection unit 3.

Next, in Step 404, the X-ray image 10 is generated based on the detected X-rays having the blur suppression pulse width.

Next, in Step 405, the device 200 reflected in the X-ray image 10 is detected from the X-ray image 10 captured by the generated X-rays having the blur suppression pulse width based on the trained model 80. That is, based on the trained model 80, the coordinate (area) indicating the position of the device 200 is detected from the X-ray image 10.

Next, in Step 406, image processing is performed on the X-ray image 10 based on the detected position (coordinate) of the device 200 to thereby generate the enhanced image 11 in which the device is enhanced.

Next, in Step 407, the generated enhanced image 11 is displayed on the display unit 5.

Effects of This Embodiment

In this embodiment, the following effects can be obtained.

According to the X-ray imaging apparatus 100 and the image processing method according to this embodiment, the pulse width of the X-rays to be emitted to generate the X-ray image 10 is set to the blur suppression pulse width that is a pulse width at which the detection accuracy of detecting the medical device 200 indwelled in the body of the subject 101 from the generated X-ray image 10 is maximized. Therefore, the device 200 can be detected based on machine learning from the X-ray image 10 generated based on the X-rays having the blur suppression pulse width. Therefore, the X-ray image 10 is captured using the X-rays having the blur suppression pulse width that is a relatively small pulse width equal to or lower than a pulse width at which the detection accuracy of detecting the device 200 is maximized. For this reason, even in a case where the device 200 within the body is irregularly moved due to the irregular movements in the body of the subject 101, it is possible to suppress a wide variety of types of blur of the device 200 reflected in the captured X-ray image 10. Accordingly, even in a case where the device 200 in the body of the subject 101 moves irregularly, the blur of the device 200 reflected in the X-ray image 10 is suppressed to be smaller than a certain size. Therefore, it is possible to suppress the decrease in the detection accuracy of detecting the device 200 based on the trained model 80. Consequently, the medical device 200 indwelled in the body of the subject 101 reflected in the X-ray image 10 can be accurately detected based on the trained model 80 generated by machine learning.

Further, in a case where the pulse width of the X-rays for generating the X-ray image 10 is set to be larger than the pulse width at which the detection accuracy of detecting the device 200 is maximized, the detection accuracy of detecting the device 200 is reduced. Further, in a case where the pulse width is increased, the dose of the X-rays emitted to the subject 101 also increases. On the other hand, in this embodiment, the X-ray image 10 is generated based on the X-rays having the blur suppression pulse width that is a pulse width equal to or lower than the pulse width at which the detection accuracy of detecting the device 200 is maximized. Therefore, since the X-ray image 10 is generated based on the X-rays having the blur suppression pulse width that is a relatively small pulse width, it is possible to suppress an increase in the dose of the X-rays emitted to the subject 101 while effectively suppressing the detection accuracy of the device 200 from becoming low. Consequently, the device 200 can be detected with higher accuracy, and the dose of the X-rays emitted to the subject 101 can be reduced.

Further, in the above-described embodiment, further effects can be obtained by configuring as follows.

That is, in this embodiment, the device detection unit 74 is configured to detect the device 200 from the X-ray image generated based on the X-rays having the blur suppression pulse width, based on the trained model 80 generated by machine learning using the training image corresponding to the X-ray image 10 generated based on the X-rays having the blur suppression pulse width. With this configuration, the trained model 80 generated by machine learning using the training image corresponding to the X-ray image 10 generated based on the X-rays having the blur suppression pulse width is used. Therefore, the device 200 reflected in the X-ray image 10 generated based on the X-rays having the blur suppression pulse width can be detected with higher accuracy.

Also, in this embodiment, the device detection unit 74 is configured to detect the device 200 from the X-ray image generated based on the X-rays having the blur suppression pulse width, based on the trained model 80 generated by machine leaning using the training input X-ray image 81 generated to simulate the device 200 in the subject 101 reflected in the X-ray image 10 generated based on the X-rays having the blur suppression pulse width and the training output information 82 indicating the position or the shape of the device 200 included in the training input X-ray image 81. With this configuration, the trained model 80 trained by using the training input X-ray image 81 simulating the device 200 reflected in the X-ray image 10 generated based on the X-rays having the blur suppression pulse width is used, and therefore, the detection accuracy of detecting the device 200 by trained model 80 can be further improved. Therefore, the device 200 reflected in the X-ray image 10 generated based on the X-rays having the blur suppression pulse width can be detected with higher accuracy.

Further, in this embodiment, the device detection unit 74 is configured to detect the device 200 from the X-ray image generated based on the X-rays having the blur suppression pulse width, based on the trained model 80 generated by machine learning using the training input X-ray image 81 generated to simulate the device 200 in the body of the subject 101 reflected in the X-ray image 10 based on the simulated X-ray image generated based on the X-rays having the blur suppression pulse width and the training output information 82 indicating the position or the shape of the device 200 reflected in the training input X-ray image 81. With this configuration, the device 200 can be detected based on the trained model 80 trained by using the training input X-ray image 81 based on the simulated X-ray image generated based on the X-ray having the blur suppression pulse width for the X-ray image 10 generated based on the X-rays having the blur suppression pulse width. That is, both the training input X-ray image 81 used for the input in the learning for generating the trained model 80 and the X-ray image 10 used for the input in the inference based on the trained model 80 each can be an image generated based on the X-rays having the blur suppression pulse width. Therefore, the input in the training of the trained model 80 and the input in the inference of the trained model 80 can be X-ray images under the same condition. Therefore, the detection accuracy of detecting the device 200 by the trained model 80 can be further improved.

Further, in this embodiment, the device 200 includes a catheter or a guidewire to be indwelled in a blood vessel in the vicinity of the heart of the subject 101. The device detection unit 74 is configured to detect a catheter or a guidewire from the X-ray image 10 generated based on the X-rays having the blur suppression pulse width, based on the trained model 80 generated by machine learning using the training input X-ray image 81 generated to simulate a catheter or a guidewire indwelled in the blood vessel in the vicinity of the heart of the subject 101 reflected in the X-ray image 10 and the training output information 82 indicating the position or the shape of the catheter or the guidewire included in the training input X-ray image 81. Here, the blood vessel in the vicinity of the heart moves largely irregularly and three-dimensionally due to the heartbeat. As a result, the catheter or the guidewire indwelled in the blood vessel in the vicinity of the heat moves irregularly and three-dimensionally due to the heartbeat, and therefore, it is considered that the catheter or the guidewire is reflected as an image with irregular and various kinds of blur in the X-ray image 10. Therefore, as in the embodiment described above, by acquiring the X-ray image 10 by causing the X-rays having the blur suppression pulse width that is a pulse width equal to or less than a predetermined threshold to emit from the X-ray irradiation unit 2, it is possible to decrease the type of blur in the X-ray image 10 even in the catheter or the guidewire indwelled in the blood vessel that moves largely irregularly due to the heartbeat. In addition, the catheter or the guidewire can be detected from the X-ray image 10 generated based on the X-rays having the blur suppression pulse width, and therefore, the visibility of the catheter or the guidewire can be improved even in a case where the catheter or the guidewire is indwelled in an organ that moves largely irregularly, such as, e.g., the blood vessel in the vicinity of the heart.

Further, in this embodiment, the blur suppression pulse width is a pulse width of 8 milliseconds (ms) or less. The device detection unit 74 is configured to detect the device 200 from the X-ray image 10 generated based on the X-rays having a pulse width of 8 milliseconds (ms) or less based on the trained model 80. With this configuration, it is possible to detect the device 200 from the X-ray image 10 in which the type of blur of the device 200 is suppressed by using the X-rays having a pulse width of 8 milliseconds (ms) or less. Therefore, the device 200 is detected based on the X-ray image 10 generated based on the X-rays having a pulse width of 8 milliseconds (ms) or less, which makes it possible to improve the detection accuracy of detecting the device 200 as compared with the case in which the pulse width is greater than 8 milliseconds (ms).

Further, in this embodiment, the device detection unit 74 is configured to detect the device 200 from the X-ray image 10 generated based on the X-rays having the blur suppression pulse width, based on the trained model 80 generated by deep learning, which is machine learning using a multi-layer neural network. With this configuration, the device 200 can be detected from the X-ray image 10 based on the trained model 80 in which an appropriate feature and an algorithm for obtaining the feature are automatically constructed by deep learning, and therefore, the detection accuracy of detecting the device 200 can be further improved.

In this embodiment, the X-ray imaging apparatus is further provided with the controller 7. The controller 7 includes: the pulse width setting unit 72 configured to set the pulse width of the X-rays emitted from the X-ray irradiation unit 2; the X-ray irradiation control unit 71 configured to cause the X-rays having the set pulse width (blur suppression pulse width) to be emitted from the X-ray irradiation unit 2; the X-ray image generation unit 73 configured to generate the X-ray image 10 based on the X-rays detected by the X-ray detection unit 3; and the device detection unit 74 configured to detect the device 200 reflected in the X-ray image 10, from the X-ray image 10 generated by the X-ray image generation unit 73, based on the trained model 80 generated by machine learning. With this configuration, it is possible to easily perform the setting of the pulse width, the emission of the X-rays, the generation of the X-ray image 10, and the detection of the device 200 by the control using software by the controller 7.

(Effects of Trained Model Generation Method by this Embodiment)

In the trained model generation method according to this embodiment, the following effects can be obtained.

In the trained model generation method of this embodiment, as described above, by acquiring the training input X-ray image 81 generated to simulate the device 200 in the body of the subject 101 reflected in the X-ray image 10 generated based on the X-rays having the blur suppression pulse width, it is possible to suppress the increase in the type of blur. Therefore, it is possible to prevent the necessity of acquiring a large number of training input X-ray images 81 to cope with various types of blur of the device 200. Here, in a case where machine learning is performed using a large number of training input X-ray images 81 to correspond to the X-ray images 10 having a wide variety of blurs, the learning is less likely to converge, and the detection accuracy by the trained model 80 is low even if the learning converges. In contrast, in this embodiment, the training input X-ray image 81 is acquired. The training input X-ray image 81 is generated to simulate the device 200 in the body of the subject 101 reflected in the X-ray image 10 generated based on the X-rays having the blur suppression pulse width. With such a configuration, as compared with the case in which the pulse width is not restricted and therefore there are a wide variety of blur of the device 200 reflected in the image, the type of blur of the X-ray image 10 acquired as a training image can be reduced. As a result, the number of types of the training input X-ray images 81 can be reduced, so that the learning can easily converge as compared with the case in which there is a wide variety of blur of the device 200, and it is possible to generate the trained model 80 capable of detecting the device 200 with high accuracy. Consequently, it is possible to provide a trained model generation method capable of accurately detecting the medical device 200 indwelled in the body of the subject 101 in the X-ray image 10.

Further, in this embodiment, as described above, the step of acquiring the training input X-ray image 81 includes: a step of acquiring simulated X-ray images (simulated human body image 81*a* and the simulated device image 81*b*)

generated based on the X-rays having the blur suppression pulse width; and a step of generating the training input X-ray image 81 to simulate the device 200 in the body of the subject 101 reflected in the X-ray image 10 by subjecting the acquired simulated X-ray image to image processing. With this configuration, the device 200 can be detected based on the trained model 80 trained by using the training input X-ray image 81 based on the simulated X-ray image generated based on the X-rays having the blur suppression pulse width for the X-ray image 10 generated based on the X-rays having the blur suppression pulse width. That is, both the training input X-ray image 81 used for the input in the learning for generating the trained model 80 and the X-ray image 10 used for the input in the inference based on the trained model 80 each can be an image generated based on the X-rays having the blur suppression pulse width. Therefore, the input in the training of the trained model 80 and the input in the inference of the trained model 80 each can be an image generated based on the X-rays of the same conditions. Therefore, the detection accuracy of detecting the device 200 by the trained model 80 can be further improved.

(Modifications)

It should be understood that the embodiments disclosed here are examples in all respects and are not restrictive. The scope of the present invention is indicated by the appended claims rather than by the description of the above-described embodiments and includes all modifications (changes) within the meanings and the scopes equivalent to the scope of the claims.

For example, in the above-described embodiment, an example is shown in which an enhanced image in which the device is enhanced is generated based on performing image processing for increasing the density of the area of the detected device, but the present invention is not limited thereto. In the present invention, the device may be emphasized by coloring the area of the detected device. Alternatively, the device may be highlighted (increased in the intensity of the outline) and displayed by highlighting the outline of the area of the detected device.

Further, in the above-described embodiment, an example is shown in which the blur suppression pulse width can be appropriately changed within the range of 8 milliseconds (ms) (predetermined threshold) or less, but the present invention is not limited thereto. In the present invention, the blur suppression pulse width may be a fixed value of a predetermined threshold or less. For example, in a case where the blur suppression pulse width is set to a pulse width having a fixed value of 5 milliseconds (ms), the X-ray imaging apparatus may be configured to capture an X-ray image generated based on the X-rays having a fixed pulse width of 5 milliseconds (ms). Further, in a case where an X-ray image is generated based on the X-rays having a pulse width of 5 milliseconds (ms), it may be configured such that the device is detected from the captured X-ray image, based on the trained model generated using the training input X-ray image generated based on a simulated X-ray image generated based on the X-rays having a pulse width of 5 milliseconds (ms) and training output information. Further, in a case where the X-ray image is generated based on the X-rays having a pulse width of 5 milliseconds (ms), it may be configured such that the device is detected from the captured X-ray image, based on the trained model generated using the training input X-ray image and the training output information generated based on the simulated X-ray image generated based on the X-rays having a plurality of pulse widths of 8 milliseconds or less, for example.

Further, in the above-described embodiment, an example is shown in which it is further provided with a controller that performs a control by software for causing the X-ray irradiation unit to emit the X-rays having the blur suppression pulse width, generating the X-ray image based on the detection signal from the X-ray detection unit, and detecting the device from the X-ray image generated based on the X-rays having the blur suppression pulse width based on the trained model generated by machine learning using the image generated to correspond to the blur suppression pulse width as a training image, but the present invention is not limited thereto. In the present invention, a controller for controlling the X-ray irradiation unit to emit the X-rays and a controller for controlling to detect the device from the X-ray image may be separately configured. For example, an image generation unit including image processing circuitry as hardware that generates an X-ray image from the detected X-rays may be configured separately from the controller. Further, an image processing module that generates an enhanced image from an X-ray image based on the position or the shape of the device acquired by using a trained model may be provided separately from the controller. That is, the pulse width setting unit, the X-ray irradiation control unit, the X-ray image generation unit, and the device detection unit may be separately configured.

Further, in the above-described embodiment, an example is shown in which the control unit (device detection unit) is configured to detect the device from the X-ray image, based on the trained model generated by machine learning using the training input X-ray image generated to simulate the device in the body of the subject reflected in the X-ray image generated based on the X-ray having the blur suppression pulse width, but the present invention is not limited thereto. In the present invention, instead of using the training input X-ray image generated to simulate the device, a trained model generated based on learning an actually captured X-ray image as teacher-input data may be used. Further, an image generated in a simulated manner without using X-rays may be used as the training input X-ray image.

Further, in the above-described embodiment, an example is shown in which the control unit (device detection unit) is configured to detect the device from the X-ray image, based on the trained model generated by machine learning using the training input X-ray image generated to simulate the device in the body of the subject reflected in the X-ray image based on the simulated X-ray image generated based on the X-rays having the blur suppression pulse width, but the present invention is not limited thereto. In the present invention, a trained model generated by machine learning using the training input X-ray image generated based on a simulated X-ray image generated based on the X-rays having a pulse width different from the blur suppression pulse width may be used.

Further, in the above-described embodiment, an example is shown in which the device includes a catheter or a guidewire indwelled in the blood vessel in the vicinity of the heart of the subject, but the present invention is not limited thereto. In the present invention, the device may be a stent and a prosthetic valve, etc., indwelled in the blood vessel in the vicinity of the heart of the subject. Further, the device may be a device to be indwelled in a blood vessel of a head.

Further, in the above-described embodiment, an example is shown in which the pulse width of a predetermined threshold or less is a pulse width of 8 milliseconds (ms) or less, but the present invention is not limited thereto. In the present invention, the pulse width of a predetermined threshold or less may be a pulse width of 5 milliseconds (ms) or less. That is, a pulse width smaller than a pulse width at which the detection accuracy of detecting the device is maximized may be set to the predetermined threshold. This makes it possible to further reduce the dose of the X-rays emitted to the subject by setting a pulse width smaller than a pulse width at which the detection accuracy of detecting the device is maximized to a predetermined threshold.

Further, in the above-described embodiment, an example is shown in which the device is detected from the X-ray image generated based on the X-rays having the blur suppression pulse width, based on the trained model generated by deep learning, which is machine learning using a multi-layer-layer neural network, but the present invention is not limited thereto. In the present invention, machine learning other than deep learning may be used. For example, SVM (support vector machine) may be used to detect the device from an X-ray image.

Further, in the above-described embodiment, an example is shown in which the device is detected from the X-ray image based on one trained model, but the present invention is not limited thereto. In the present invention, the device may be detected from an X-ray image based on a plurality of trained models.

Further, in the above-described embodiment, an example is shown in which a trained model generated to detect the position (coordinate) of the device reflected in the X-ray image is used, but the present invention is not limited thereto. The present invention may use a trained model generated to detect the shape (coordinate) of the device reflected in the X-ray image. That is, a trained model generated by machine learning based on the training output information indicating the shape (contour) of the device reflected in the training input X-ray image may be used. For example, a trained model trained by machine learning may be used as training data (training set) using an training input X-ray image that is an image including an object having a form such as a shape corresponding to a device reflected in an X-ray image and a training output information that is a shape (contour) specified by specifying a shape of an object corresponding to a device reflected in a training input X-ray image.

Aspects

It will be understood by those skilled in the art that the above-described exemplary embodiments are concrete examples of the following aspects.

(Item 1)

An X-ray imaging apparatus comprising:
an X-ray irradiation unit configured to irradiate a subject in which a medical device is indwelled with X-rays;
an X-ray detection unit configured to detect the X-rays transmitted through the subject;
a pulse width setting unit configured to set a pulse width of the X-rays emitted from the X-ray irradiation unit;
an X-ray irradiation control unit configured to cause X-rays having the pulse width set by the pulse width setting unit to emit from the X-ray irradiation unit;
an X-ray image generation unit configured to generate an X-ray image based on the X-rays detected by the X-ray detection unit, the X-rays having the set pulse width; and
a device detection unit configured to detect the device in the X-ray image, based on a trained model generated by machine learning, from the X-ray image generated by the X-ray generation unit, the X-ray image being generated based on the X-rays having the set pulse width,
wherein the pulse width is a blur suppression pulse width equal to or less than a pulse width at which detection accuracy of detecting the device based on the trained model is maximized.

(Item 2)

The X-ray imaging apparatus as recited in the above-described Item 1,
wherein the device detection unit is configured to detect the device, based on the trained model generated by machine learning using a training image corresponding to the X-ray image generated based on the X-rays having the blur suppression pulse width, from the X-ray image generated based on the X-rays having the blur suppression pulse width.

(Item 3)

The X-ray imaging apparatus as recited in the above-described Item 2,
wherein the device detection unit is configured to detect the device from the X-ray image generated based on the X-rays having the blur suppression pulse, based on the trained model generated by machine learning using a training input X-ray image and training output information, the training input X-ray image being generated to simulate the device in a body of the subject reflected in the X-ray image generated based on the X-rays having the blur suppression pulse width, the training output information indicating a position or a shape of the device reflected in the training input X-ray image.

(Item 4)

The X-ray imaging apparatus as recited in the above-described Item 3,
wherein the device detection unit is configured to detect the device from the X-ray image generated based on the X-rays having the blur suppression pulse, based on the trained model generated by machine learning using the training input X-ray image and the training output information, the training input X-ray image being generated to simulate the device in the body of the subject reflected in the X-ray image based on a simulated X-ray image generated based on the X-rays having the blur suppression pulse width, the training output information indicating the position or the shape of the device reflected in the training input X-ray image.

(Item 5)

The X-ray imaging apparatus as recited in the above-described Item 3,
wherein the device includes a catheter or a guidewire to be indwelled in a blood vessel in the vicinity of a heart of the subject, and
wherein the device detection unit is configured to detect the catheter or the guidewire from the X-ray image generated based on the X-rays having the blur suppression pulse width, based on the trained model generated by machine learning using the training input X-ray image and the training output information, the training input X-ray image being generated to simulate the catheter or the guidewire indwelled in the blood vessel in the vicinity of the heart of the subject reflected in the X-ray image, the training output information indicating the position or the shape of the catheter or the guidewire reflected in the training input X-ray image.

(Item 6)

The X-ray imaging apparatus as recited in the above-described Item 1,
wherein the blur suppression pulse width is a pulse width of 8 milliseconds (ms) or less, and wherein the device detection unit is configured to detect the device from the X-ray image generated based on the X-rays having a pulse width of 8 milliseconds (ms) or less, based on the trained model.

(Item 7)

The X-ray imaging apparatus as recited in the above-described Item 1,
wherein the device detection unit is configured to detect the device from the X-ray image generated based on the X-rays having the blur suppression pulse width, based on the trained model generated by deep learning that is machine learning using a multi-layer neural network.

(Item 8)

The X-ray imaging apparatus according to the above-described Item 1, further comprising:
a controller,
wherein the controller includes:
the pulse width setting unit configured to set the pulse width of the X-rays emitted from the X-ray irradiation unit;
the X-ray irradiation control unit configured to cause the X-rays having the set pulse width to emit from the X-ray irradiation unit;
the X-ray image generation unit configured to generate the X-ray image based on the X-rays detected by the X-ray detection unit; and
the device detection unit configured to detect the device reflected in the X-ray image, based on the trained model generated by machine learning, from the X-ray image generated by the X-ray image generation unit.

(Item 9)

A trained model generation method comprising the steps of:
acquiring a training input X-ray image, the training input X-ray image being generated to simulate a medical device to be indwelled in a body of a subject in an X-ray image generated based on the X-rays having a blur suppression pulse width equal to or less than a pulse width at which detection accuracy of detecting the medical device is maximized such that the training input X-ray image corresponds to the X-ray image generated based on the X-rays having the blur suppression pulse width;
acquiring training output information indicating a position or a shape of the device in the training input X-ray image; and
generating a trained model by machine learning using the training input X-ray image and the training output information.

(Item 10)

The trained model generation method as recited in the above-described Item 9,
wherein the step of acquiring the training input X-ray image includes the steps of:
acquiring a simulated X-ray image generated based on the X-rays having the blur suppression pulse width; and
generating the training input X-ray image to simulate the device in the body of the subject reflected in the X-ray image by subjecting the acquired simulated X-ray image to image processing (Item 11)

An image processing method, comprising the steps of:
setting a pulse width of X-rays emitted to generate an X-ray image to a blur suppression pulse width, the blur suppression pulse width being equal to or less than a pulse width at which detection accuracy of detecting a medical device indwelled in a body of a subject from the generated X-ray image based on a trained model generated by machine learning is maximized;
irradiating the subject in which the device is indwelled with the X-rays having the set blur suppression pulse width;
detecting the X-rays transmitted through the subject;
generating the X-ray image based on the detected X-rays having the blur suppression pulse width; and
detecting the device in the X-ray image based on the trained model from the X-ray image generated based on the X-rays having the blur suppression pulse width.

Other Aspects

The embodiments described above may also be a specific example of the following aspect.

(Item 12)

A method of improving the image quality of a short-time exposure X-rays for a movable object (device) in a human body, comprising:
emitting one or more bursts (irradiations) of X-rays toward the movable object in the human body, wherein the one or more bursts of X-rays include at least one burst of X-rays of a short exposure (pulse width) having an exposure period shorter than an exposure period (pulse width) of a predetermined threshold;
detecting one or more bursts of X-rays;
generating a low-resolution X-ray image of the movable object in the human body, based on the one or more bursts of X-rays;
generating a contour of the movable object reflected in a low-resolution X-ray image by inputting the low-resolution X-ray image to one or more machine learning models (trained models), wherein each of the one or more machine learning models is trained (learned) according to a training set (training data) including an X-ray image (training input X-ray image) of an object having a shape and a material corresponding to the movable object reflected in the low-resolution X-ray image and a specified contour (training output information) of the object reflected in the X-ray image (training input X-ray image); and
generating and outputting a new X-ray image (enhanced image) based on the low-resolution X-ray image by increasing the intensity of the generated contour of the movable object, wherein the new X-ray image is high in resolution of the movable object than the low-resolution X-ray image.

(Item 13)

A device for improving the image quality of a short-time exposure X-rays for a movable object (device) in a human body, comprising:
an X-ray generator (X-ray irradiation unit) configured to generate one or more bursts of X-rays and emit the one or more bursts of X-rays to the movable object in the human body, wherein the one or more bursts of X-rays include at least one short-exposure (pulse width) burst of X-rays having an exposure period shorter than a predetermined threshold exposure period (pulse width):
an X-ray detector (X-ray detection unit) configured to detect the one or more bursts of X-rays;
an image generation unit configured to generate a low-resolution X-ray image of the movable object in the human body, based on the one or more bursts of X-rays;
one or more trained machine learning systems configured to generate a contour of the movable object in the low-resolution X-ray image by inputting the low-resolution X-ray image to one or more machine learning models (trained models), wherein each of the one or more machine learning models is trained (learned) according to a training set (training data) including an X-ray image (training input X-ray image) of the object having a shape and a material corresponding to the movable object reflected in the low-resolution X-ray image and a specified contour (training output information) of the object reflected in the X-ray image (training input X-ray image);

an image processing module configured to generate and output a new X-ray image (enhanced image) based on the low-resolution X-ray image by increasing the intensity of the generated contour of the movable object, wherein the new X-ray image is higher in the resolution of the movable object than that of the low-resolution X-ray image.

Item 14

A training (learning) method of a machine learning model (trained model) for improving the image quality of a short-time exposure X-ray for a movable object (device), the method comprising:

acquiring a plurality of X-ray images (training input X-ray images) depicted by a contour of an object having a shape and a material corresponding to the movable object (device), wherein the plurality of X-ray images includes at least one X-ray image including a contour depicted with a low-resolution; and training one or more machine learning models using a plurality of X-ray images (training input X-ray images) and a contour line (training output information) and correlating the X-ray image (training input X-ray image) with the contour (training output information) of the object having the shape and the material corresponding to the movable object of the X-ray image (training input X-ray image).

DESCRIPTION OF SYMBOLS

2: X-ray irradiation unit
3: X-ray detection unit
7: Controller
10: X-ray Image
71: X-ray irradiation control unit
72: Pulse width setting unit
73: X-ray image generation unit
74: Device detection unit
80: Trained model
81: Training input X-ray image
82: Training output information
100: X-ray imaging apparatus
101: Subject
200: Device

The invention claimed is:

1. An X-ray imaging apparatus comprising:
an X-ray irradiation unit configured to irradiate a subject in which a medical device is indwelled with X-rays;
an X-ray detection unit configured to detect the X-rays transmitted through the subject;
a pulse width setting unit constituted by a processor configured to set a pulse width of the X-rays emitted from the X-ray irradiation unit;
an X-ray irradiation control unit constituted by the processor configured to cause X-rays having the pulse width set by the pulse width setting unit to emit from the X-ray irradiation unit;
an X-ray image generation unit constituted by the processor configured to generate an X-ray image based on the X-rays detected by the X-ray detection unit, the X-rays having the set pulse width; and
a device detection unit constituted by the processor configured to detect the medical device in the X-ray image, based on a trained model generated by machine learning, from the X-ray image generated by the X-ray image generation unit, the X-ray image being generated based on the X-rays having the set pulse width,
wherein the pulse width is a blur suppression pulse width equal to or less than a pulse width at which detection accuracy of detecting the medical device based on the trained model is maximized.

2. The X-ray imaging apparatus as recited in claim 1, wherein the device detection unit is configured to detect the medical device, in the X-ray image generated based on the X-rays having the blur suppression pulse width, the device detection unit being configured to detect the medical device based on the trained model generated by machine learning using a training image corresponding to the X-ray image generated based on the X-rays having the blur suppression pulse width.

3. The X-ray imaging apparatus as recited in claim 2, wherein the device detection unit is configured to detect the medical device from the X-ray image generated based on the X-rays having the blur suppression pulse, based on the trained model generated by machine learning using a training input X-ray image and training output information, the training input X-ray image being generated to simulate the medical device in a body of the subject reflected in the X-ray image generated based on the X-rays having the blur suppression pulse width, the training output information indicating a position or a shape of the medical device reflected in the training input X-ray image.

4. The X-ray imaging apparatus as recited in claim 3, wherein the device detection unit is configured to detect the medical device from the X-ray image generated based on the X-rays having the blur suppression pulse, based on the trained model generated by machine learning using the training input X-ray image and the training output information, the training input X-ray image being generated to simulate the medical device in the body of the subject reflected in the X-ray image based on a simulated X-ray image generated based on the X-rays having the blur suppression pulse width, the training output information indicating the position or the shape of the medical device reflected in the training input X-ray image.

5. The X-ray imaging apparatus as recited in claim 3, wherein the medical device includes a catheter or a guidewire to be indwelled in a blood vessel in the vicinity of a heart of the subject, and
wherein the device detection unit is configured to detect the catheter or the guidewire from the X-ray image generated based on the X-rays having the blur suppression pulse width, based on the trained model generated by machine learning using the training input X-ray image and the training output information, the training input X-ray image being generated to simulate the catheter or the guidewire indwelled in the blood vessel in the vicinity of the heart of the subject reflected in the X-ray image, the training output information indicating the position or the shape of the catheter or the guidewire reflected in the training input X-ray image.

6. The X-ray imaging apparatus as recited in claim 1,
wherein the blur suppression pulse width is a pulse width of 8 milliseconds (ms) or less, and
wherein the device detection unit is configured to detect the medical device from the X-ray image generated based on the X-rays having a pulse width of 8 milliseconds (ms) or less, based on the trained model.

7. The X-ray imaging apparatus as recited in claim 1,
wherein the device detection unit is configured to detect the medical device from the X-ray image generated based on the X-rays having the blur suppression pulse width, based on the trained model generated by deep learning that is machine learning using a multi-layer neural network.

8. The X-ray imaging apparatus according to claim 1, further comprising:
a controller,
wherein the controller includes:
the pulse width setting unit configured to set the pulse width of the X-rays emitted from the X-ray irradiation unit;
the X-ray irradiation control unit configured to cause the X-rays having the set pulse width to emit from the X-ray irradiation unit;
the X-ray image generation unit configured to generate the X-ray image based on the X-rays detected by the X-ray detection unit; and
the device detection unit configured to detect the medical device reflected in the X-ray image, based on the trained model generated by machine learning, from the X-ray image generated by the X-ray image generation unit.

9. A trained model generation method comprising the steps of:
acquiring a training input X-ray image, the training input X-ray image being generated to simulate a medical device to be indwelled in a body of a subject in an X-ray image generated based on the X-rays having a blur suppression pulse width equal to or less than a pulse width at which detection accuracy of detecting the medical device is maximized such that the training input X-ray image corresponds to the X-ray image generated based on the X-rays having the blur suppression pulse width;
acquiring training output information indicating a position or a shape of the medical device in the training input X-ray image; and
generating a trained model by machine learning using the training input X-ray image and the training output information.

10. The trained model generation method as recited in claim 9,
wherein the step of acquiring the training input X-ray image includes the steps of:
acquiring a simulated X-ray image generated based on the X-rays having the blur suppression pulse width; and
generating the training input X-ray image to simulate the medical device in the body of the subject reflected in the X-ray image by subjecting the acquired simulated X-ray image to image processing.

11. An image processing method comprising the steps of:
setting a pulse width of X-rays emitted to generate an X-ray image to a blur suppression pulse width, the blur suppression pulse width being equal to or less than a pulse width at which detection accuracy of detecting a medical device indwelled in a body of a subject, in the generated X-ray image, is maximized, based on a trained model generated by machine learning;
irradiating the subject in which the medical device is indwelled with the X-rays having the set blur suppression pulse width;
detecting the X-rays transmitted through the subject;
generating the X-ray image based on the detected X-rays having the blur suppression pulse width; and
detecting the medical device in the X-ray image based on the trained model from the X-ray image generated based on the X-rays having the blur suppression pulse width.

* * * * *